United States Patent [19]

Pellacini et al.

[11] Patent Number: 5,866,604
[45] Date of Patent: Feb. 2, 1999

[54] THIOL DERIVATIVES WITH METALLOPEPTIDASE INHIBITORY ACTIVITY

[75] Inventors: Franco Pellacini, Milan; Stefano Romagnano, Buccinasco; Gabriele Norcini, Vizzola Ticino; Francesco Santangelo, Milan, all of Italy

[73] Assignee: Zambon Group S.p.A., Milan, Italy

[21] Appl. No.: 750,995

[22] PCT Filed: Jan. 23, 1996

[86] PCT No.: PCT/EP96/00251

§ 371 Date: Dec. 24, 1996

§ 102(e) Date: Dec. 24, 1996

[87] PCT Pub. No.: WO96/22998

PCT Pub. Date: Aug. 1, 1996

[30] Foreign Application Priority Data

Jan. 27, 1995 [IT] Italy .................................. MI95A0132

[51] Int. Cl.$^6$ ...................... C07C 327/32; C07C 323/60; A61K 38/55; C07K 5/06

[52] U.S. Cl. ............................. 514/506; 560/10; 560/16; 560/147; 560/9; 562/426; 562/489; 562/490; 562/556; 562/564; 514/506; 514/562

[58] Field of Search ...................................... 562/426, 489, 562/490, 556, 564; 514/506, 562; 560/9, 10, 16, 147

[56] References Cited

U.S. PATENT DOCUMENTS

| | | | |
|---|---|---|---|
| 4,053,651 | 10/1977 | Ondetti et al. | 424/319 |
| 4,199,512 | 4/1980 | Ondetti et al. | 260/326.12 R |
| 4,316,896 | 2/1982 | Thorsett et al. | 424/200 |
| 4,379,146 | 4/1983 | Greenlee et al. | 424/177 |
| 4,432,972 | 2/1984 | Karanewsky et al. | 424/177 |
| 5,151,414 | 9/1992 | Casagrande et al. | 514/114 |
| 5,451,608 | 9/1995 | Santangelo et al. | 514/674 |

FOREIGN PATENT DOCUMENTS

| | | | |
|---|---|---|---|
| 9308162 | 4/1993 | WIPO | C07C 323/51 |
| 9535315 | 12/1995 | WIPO | C07K 5/062 |

OTHER PUBLICATIONS

Derpez et al., Bioorganic & Medicinal Chemistry Letters, vol. 6, No. 19, pp. 2317–2322, 1996.

Bhagwat et al., Bioorganic & Medicinal Chemistry Letters, vol. 5, No. 7, pp. 735–738, 1995.

Merz et al., "Free Energy Perturbation Simulations of the Inhibition of Thermolysin: Prediction of the Free Energy of Binding of a New Inhibitor", *J. Am. Chem. Soc.*, vol. 111, No. 15 (1989), pp. 5649–5658.

Mookhtiar, K.A. et al., "Phosphonamidate Inhibitors of Human Neutrophil Collagenase". *Biochemistry*, vol. 26, No. 7 (1987), pp. 1962–1965.

McMahon et al., "Phosphoramidon Blocks the Pressor Activity of Porcine Big Endothelin–1–(1–39) In Vivo and Conversion of Big Endothelin–1–(1–39), 2 Endothelin–1–(1–21) In Vitro", *Proceedings National Academy of Science*, vol. 88 (Feb. 1991), pp. 703–707.

Fukuroda, T. et al., "Inhibition of Biological Action of Big Endothelin–1 by Phosphoramidon", *Biochemical and Biophysical Research Communication*, vol. 172, No. 2 (Oct. 30, 1990), pp. 390–395.

Rich, H. David, "Peptidase Inhibitors" in *Comprehensive Medicinal Chemistry: The Rational Design, Mechanistic Study & Therapeutic Application of Chemical Compounds*, vol. 2 (Pergamon Press PLC), pp. 391–496 (not continuous), 1990.

Kam, C.M. et al., "Inhibition of Thermolysin and Carboxy Peptidase A Biphosphoramides", *Biochemistry*, vol. 18, No. 14 (1979), pp. 3032–3038.

*Primary Examiner*—S. Mark Clardy
*Assistant Examiner*—Sabiha N. Qazi
*Attorney, Agent, or Firm*—Nikaido, Marmelstein, Murray & Oram, LLP

[57] ABSTRACT

Compounds of formula (I) wherein R, $R_1$, $R_2$, $R_3$, $R_4$, m and n have the meanings reported in the description, processes for their preparation and pharmaceutical compositions which contain them as active ingredients are described. The compounds of formula (I) are endowed with a mixed ACE-inhibitory and NEP-inhibitory activity and are useful in the treatment of cardiovascular diseases.

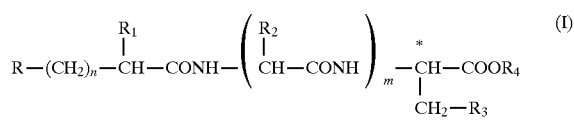

7 Claims, No Drawings

THIOL DERIVATIVES WITH METALLOPEPTIDASE INHIBITORY ACTIVITY

This application has been filed under 35 USC 371 as a national stage application of PCT/EP96/00251, filed Jan. 23, 1996, published as WO96/22998 Aug. 1, 1996.

The present invention relates to thiol derivatives with metallopeptidase inhibitory activity and, more particularly, it relates to mercaptoacylamino derivatives useful in the treatment of cardiovascular diseases.

The pharmacologic interest towards the study of metallopeptidase inhibitory molecules derives from the role that said enzymes exert on the level of the cardiocirculatory system.

It is well-known, in fact, that compounds with angiotensin converting enzyme (ACE) inhibitory activity are mainly useful in the treatment of hypertension and of heart failure in that they inhibit the formation of angiotensin II, a substance which increases the blood pressure.

Compounds with endothelin converting enzyme (ECE) inhibitory activity are useful as anti-vasoconstrictors in that they inhibit the formation of endothelin, a 21 amino acid peptide with vasoconstrictor activity.

Instead, compounds with inhibitory activity of the neutral endopeptidase enzyme (NEP), also called enkephalinase, are useful as vasodilators in that the NEP enzyme is responsible for the inactivation, not only of endogenous enkephaline, but also of atrial natriuretic factor (ANF), a hormone secreted by heart which increases the vasodilation and, on the renal level, increases diuresis and natriuresis.

Therefore, even exerting their action on the cardiovascular system with different mechanisms of action, the compounds with metallopeptidase inhibitory activity are generally used, alone or in combination, in the treatment of hypertension, renal failure, congestive heart failure and ischemic cardiopathologies.

Among the metallopeptidase inhibitors having a mercaptoacylamino structure. Thiorphan [(DL-(3-mercapto-2-benzylpropanoyl)glycine], described for the first time by Roques et al. in Nature, Vol. 288, pages 286–288, (1980), and Captopril (The Merck Index, XI ed., No. 1773, page 267) are considered the parent compounds for NEP-inhibitors and ACE-inhibitors, respectively.

Other molecules with a mercaptoacylamino structure endowed with metallopeptidase inhibitory activity are described in the literature.

The U.S. Pat. No. 4,401,677 (E. R. Squibb & Sons, Inc.) describes mercaptoalkanoyl amino acids endowed with enkephalinase inhibitory activity.

The European patent application No. 0 566 157 (Schering Corporation) describes mercaptoalkanoyl amino acids endowed with neutral metalloendopeptidase inhibitory activity.

The European patent application No. 0 419 327 (Société Civile Bioproject) describes amino acid derivatives endowed with enkephalinase and ACE inhibitory activity.

The European patent application No. 0 449 523 (E.R. Squibb & Sons, Inc.) describes mercapto or acylthio trifluoromethylamides with NEP-inhibitory activity.

The international patent application No. WO 93/08162 [Rhone-Poulenc Rorer S.A.—Institut National de la Santé et de la Recherche Médicale (INSERM)] describes β,β-disubstituted α-mercaptomethylpropionylamides endowed with a mixed ACE/NEP inhibitory activity.

Among the compounds described in the patent application No. WO 93/08162, the compound known with the abbreviation RB 105 [N-[2-(mercaptomethyl)-3-phenylbutanoyl]-L-alanine] is under study as mixed ACE/NEP inhibitor for the treatment of cardiovascular diseases [Foumié-Zaluski M. C. et al., Proc. Natl. Acad. Sci. USA, vol. 91, pages 4072–4076, (1994)]. The European patent application No. 0 524 553 [Institut National de la Santé et de la Recherche Médicale (ISERM)] describes acylmercaptoalkanoyldipeptides endowed with neutral endopeptidase and peptidyldipeptidase A inhibitory activity.

Now we have found mercaptoacylamino derivatives which are endowed with a remarkable inhibitory activity on the angiotensin converting enzyme as well as on the neutral endopeptidase enzyme (mixed or dual ACE/NEP inhibitory activity) which makes them particularly useful in the cardiovascular therapy.

Therefore, object of the present invention are the compounds of formula

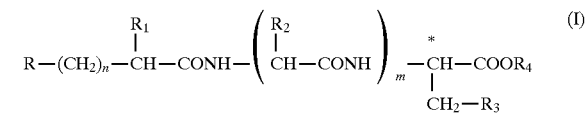

wherein

R is a mercapto group or a $R_5COS$ group convertible in the organism to mercapto group;

$R_1$ is a hydrogen atom, a straight or branched $C_1$–$C_6$ alkyl group, an aryl or an arylalkyl group having from 1 to 6 carbon atoms in the straight alkyl moiety wherein the aryl is a phenyl, a biphenyl, a naphthyl or a 5 or 6 membered aromatic heterocycle with one or two heteroatoms selected among nitrogen, oxygen and sulphur, optionally substituted with one or more substituents, the same or different, selected among halogen atoms, hydroxy groups, alkoxy, alkyl, alkylthio, alkylsulphonyl or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, mono- or di-alkylaminocarbonyl groups having from 1 to 6 carbon atoms in the alkyl moiety;

$R_2$ is a hydrogen atom, a straight or branched $C_1$–$C_6$ alkyl group or an arylalkyl group having from 1 to 6 carbon atoms in the alkyl moiety wherein the aryl is a phenyl, a biphenyl, a naphthyl or a 5 or 6 membered aromatic heterocycle with one or two heteroatoms selected among nitrogen, oxygen and sulphur, optionally substituted with one or more substituents, the same or different, selected among halogen atoms, hydroxy groups, alkoxy, alkyl, alkylthio, alkylsulphonyl or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, mono- or di-alkylaminocarbonyl groups having from 1 to 6 carbon atoms in the alkyl moiety;

$R_3$ is a biphenyl group optionally substituted with one or more substituents, the same or different, selected among halogen atoms, hydroxy groups, alkoxy, alkyl, alkylthio or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, mono- or di-alkylaminocarbonyl groups having from 1 to 6 carbon atoms in the alkyl moiety;

$R_4$ is a hydrogen atom, a $C_1$–$C_4$ alkyl group or a benzyl group;

$R_5$ is a $C_1$–$C_4$ alkyl group or a phenyl group;

m is 1 or 1;

n is 0 or 1;

the carbon atom marked with an asterisk is a stereogenic centre;

and pharmaceutically acceptable salts thereof.

Object of the present invention are the compounds of formula I in the form of stereoisomeric mixture as well as in the form of single stereoisomers.

The compounds of formula I object of the present invention are endowed with a mixed ACE-inhibitory and NEP-inhibitory activity and are useful in the treatment of cardiovascular diseases.

In the present description, unless otherwise specified, with the term biphenyl group we intend a 2-biphenyl, 3-biphenyl or 4-biphenyl group; with the term alkyl group we intend a straight or branched alkyl such as methyl, ethyl, n.propyl, isopropyl, n.butyl, sec-butyl, tert-butyl, isobutyl, n.pentyl, 2-pentyl, 3-pentyl, isopentyl, tert-pentyl, n-hexyl and iso-hexyl; with the term halogen atom we intend a fluorine, chlorine, bromine or iodine atom; with the term acyl we intend an acyl group deriving from an aliphatic or aromatic carboxylic acid such as acetic, propionic, butyric and benzoic acid; with the term aryl we intend an aromatic group such as phenyl, 2-biphenyl, 3-biphenyl, 4-biphenyl, 1-naphthyl and 2-naphthyl or a heterocyclic group containing 1 or 2 heteroatoms selected among nitrogen, oxygen and sulphur such as thiazole, isoxazole, oxazole, isothiazole, pyrazole, imidazole, thiophene, pyrrole, pyridine, pyrimidine and furan, optionally benzocondensed.

Examples of pharmaceutically acceptable salts of the compounds of formula I are the salts with alkali or alkali-earth metals and the salts with mineral acids.

Preferred compounds of formula I are the compounds wherein $R_3$ is a 4-biphenyl group optionally substituted with from 1 to 3 substituents, the same or different, selected among halogen atoms, hydroxy groups, alkoxy groups and alkyl groups; $R_1$ is a phenylalkyl group optionally substituted with one or more substituents, the same or different, selected among halogen atoms, hydroxy groups, alkoxy groups and alkyl groups; $R_4$ is a hydrogen atom; m is 0 and n is 1.

Still more preferred compounds of formula I are the compounds wherein R is a mercapto group; $R_3$ is a 4-biphenyl group optionally substituted with from 1 to 3 substituents, the same or different, selected among fluorine atoms or hydroxy groups; $R_1$ is a phenylmethyl group optionally substituted with one or more substituents, the same or different, selected among halogen atoms, hydroxy groups, alkoxy groups and alkyl groups; $R_4$ is a hydrogen atom; m is 0 and n is 1.

Another class of preferred compounds of formula I are the compounds wherein R is a mercapto group; $R_3$ is a 4-biphenyl group optionally substituted with from 1 to 3 substituents, the same or different, selected among halogen atoms, hydroxy groups, alkoxy groups and alkyl groups; $R_1$ is an arylalkyl group wherein the aryl group is a 5 or 6 membered aromatic heterocycle with one or two heteroatoms selected among nitrogen, oxygen and sulphur, optionally substituted with one or more substituents, the same or different, selected among alkyl groups; $R_4$ is a hydrogen atom; m is 0 and n is 1.

Preferred examples of pharmaceutically acceptable salts of the compounds of formula I are the salts with alkali metals such as sodium, lithium and potassium and the salts with mineral acids such as hydrochloric and hydrobromic acid.

It is clear that the compounds of formula I wherein R is a $R_5$COS group convertible in the organism to mercapto group and the compounds of formula I wherein $R_4$ is a $C_1$–$C_4$ alkyl group or a benzyl group are biologic precursors (pro-drugs) of the corresponding compounds of formula I wherein R is a mercapto group (R=SH) or $R_4$ is a hydrogen atom ($R_4$ respectively.

The preparation of the compounds of formula 1, object of the present invention, comprises the reaction between a compound of formula

wherein

R, $R_1$ and n have the above reported meanings;

and a biphenylalanine derivative of formula

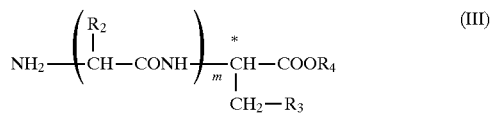

wherein $R_2$, $R_3$, $R_4$ and m have the above reported meanings.

The condensation is carried out according to conventional techniques of the chemistry of peptides.

Before carrying out the reaction, it can be useful to properly protect the eventual functional groups which could interfere in the reaction.

The optional protection is carried out according to conventional techniques.

In this respect, the compounds wherein R is a $R_5$COS group are preferably used as intermediates of formula II, thus obtaining the corresponding compounds of formula I wherein R=$R_5$COS from which, by hydrolysis, the compounds of formula I wherein R=SH can be obtained.

The evaluation of the usefulness of the optional protection as well as the selection of the kind of adopted protection, according to the reaction to be carried out and to the functional groups to be protected, are within the normal knowledge of the man skilled in the art.

The removal of the optional protective groups is carried out according to conventional techniques.

For a general reference to the use of protective groups in organic chemistry see Theodora W. Greene and Peter G. M. Wuts "Protective Groups in Organic Synthesis", John Wiley & Sons, Inc., II Ed., 1991.

The compounds of formula II are known compounds or easily prepared according to conventional methods.

For instance, the compounds of formula II can be prepared as reported in British patent No. 1,576,161 (E.R. Squibb & Sons Inc.) or, alternatively, according to the synthetic method described by M. C. Fournié-Zalusky et al. in J. Med. Chem. 1994, 37, 1070–1083.

Also the intermediates of formula III are known or easily prepared according to known methods.

For a bibliographic reference to the preparation of the compounds of formula III see, for instance, Michel Sy et al., Bull. Soc. Chim. Fr., 1276–1277, (1963) and Moses Lee et al., J. Org. Chem., 53(9), 1855–1859, (1988).

The compounds of formula I in the form of single stereoisomers are prepared by stereoselective synthesis or by separation of the stereoisomeric mixture according to conventional techniques.

Also the preparation of the salts of the compounds of formula I, object of the invention, is carried out according to conventional techniques.

The compounds of formula I object of the present invention are endowed with a mixed ACE-inhibitory and NEP-inhibitory activity and are useful in the treatment of cardiovascular diseases.

The inhibitory activity of the compounds of formula I was evaluated by means of in vitro tests in comparison to the aforementioned Thiorphan, Captopril and RB 105.

The activity of the compounds of formula I, expressed as $IC_{50}$ (nM) or as percentage of inhibition, is pharmacologically significant in comparison to the NEP-inhibitory activity of Thiorphan as well as in comparison to the ACE-inhibitory activity of Captopril.

Furthermore, the mixed ACE/NEP-inhibitory activity of the compounds of formula I, object of the present invention, is comparable or better than that of the mixed ACE/NEP inhibitor RB 105 (example 3).

The compounds of formula I, moreover, confirmed their mixed ACE/NEP-inhibitory activity also by means of ex vivo tests.

The ex vivo ACE/NEP-inhibitory activity of the compounds of formula I, in particular, was evaluated by considering the enzymatic activity in tissue homogenates (lung and kidney for the ACE- and NEP-inhibitory activity, respectively) from spontaneously hypertensive rats (SHR), 5 minutes after i.v. injection (0.64 $\mu$moles/Kg) of the tested compounds.

For instance, in the following table are reported the percentages of inhibition of the basal enzymatic activity ex vivo after i.v. administration of N-(2-mercaptomethyl-3-phenylpropionyl)-(1,1'-biphenyl-4-yl)-L-alanine, a compound representative of the class of compounds of formula I, object of the present invention.

TABLE 1

| i. v. injection | ACE-inhibitory activity (lung) | NEP-inhibitory activity (kidney) |
| --- | --- | --- |
| 0.64 $\mu$moles/Kg | 49% | 20% |

For a practical use in therapy, the compounds of formula I can be formulated in solid or liquid pharmaceutical compositions, suitable to oral or parenteral administration.

Therefore, the pharmaceutical compositions containing a therapeutically effective amount of a compound of formula I in admixture with a carrier for pharmaceutical use are a further object of the present invention.

Specific examples of pharmaceutical compositions according to the present invention are tablets, coated tablets, capsules, granulates, solutions and suspensions suitable to oral administration, solutions and suspensions suitable to parenteral administration.

The pharmaceutical compositions object of the present invention are prepared according to conventional techniques.

The daily dose of the compound of formula I will depend on different factors such as the seriousness of the disease, the individual response of the patient or the kind of formulation but it is usually comprised between 0.1 mg and 10 mg per Kg of body weight divided into a single dose or into more daily doses.

With the aim of illustrating the present invention, without limiting it, the following examples are now given.

Unless otherwise specified, the flash chromatographies were carried out by using flash chromatography silica gel from Baker company (code 7024-00) and the thin layer chromatographies (TLC) were carried out by using "silica gel plates 60 $F_{254}$" from Merck company (code 1.05719).

EXAMPLE 1

Preparation of N-[3-phenylcarbonylthio-2-(phenylmethyl)propionyl]-(1,1'-biphenyl-4-yl)-L-alanine phenylmethyl ester A solution of hydroxybenzotriazole (1.1 g; 8.15 mmoles) in tetrahydrofuran (30 ml) and, subsequently, a solution of dicyclohexylcarbodiimide (2.02 g; 9.78 mmoles) in methylene chloride (15 ml) were added, at 0° C. under stirring, to a mixture of 3-phenylcarbonylthio-2-(phenylmethyl) propionic acid (2.5 g; 8.15 mmoles), (1,1'-biphenyl-4-yl)-L-alanine methyl ester hydrochloride (3 g; 8.15 mmoles) and triethylamine (1.14 ml; 8.15 mmoles) in tetrahydrofuran (20 ml) and methylene chloride (30 ml).

The reaction mixture was kept under stirring for 20 hours, then dicyclohexylurea was filtered off and the solvent was evaporated at reduced pressure.

The residue was collected with ethyl acetate and the solution was washed with aqueous solutions of citric acid at 10%, sodium chloride at 20%, sodium bicarbonate at 5% and sodium chloride at 20% again.

After separation of the phases and evaporation of the organic phase, the resultant white solid (6 g) was purified by flash chromatography (silica gel, eluent ethyl acetate:hexane=25:75, pressure of nitrogen=0.1 atm) affording the title compound (4.2 g).

m.p. 103°–105° C.

$^1$H-NMR (200 MHz, $CDCl_3$): $\delta$ (ppm): 7.98–6.53 (m, 24H, 5Ar); 5.95–5.75 (2d, 11H, 2NH); 5.10–4.98 (m, 2H, $COOCH_2$); 4.95–4.78 (m, 1H, CHCOO); 3.35–2.60 (m, 7H, $SCH_2CHCH_2$ and $CH_2$-biphenyl).

$[M-H]^+=613$;

By working in an analogous way the following compounds were prepared:

N-[2-acetylthiomethyl-3-(3-methoxyphenyl)propionyl]-(1,1'-biphenyl-4-yl)-L-alanine methyl ester from which the two stereoisomers were separated by flash chromatography (silica gel, eluent ethyl acetate:hexane=25:75, pressure of nitrogen=0.1 atm)

Stereoisomer A m.p. 109°–110° C.

TLC (ethyl acetate:hexane=30:70) $R_f$=0.18

$^1$H-NMR (200 MHz, $CDCl_3$): $\delta$ (ppm): 7.55–6.65 (m, 13H, 3Ar); 5.78 (d, 1H, NH); 4.85–4.72 (m, 1H, CHCOO); 3.73 (s, 3H, $OCH_3$); 3.62 (s, 3H, $COOCH_3$); 3.20–2.71 (m, 6H, $SCH_2CHCH_2$ and $CH_2$-biphenyl); 2.63–2.49 (m, 1H, $CH_2CHCH_2$); 2.29 (s, 3H, CH COS)

$[M-H]^+=506$;

N-[2-acetylthiomethyl-3-(3-methoxyphenyl)propionyl]-(1,1'-biphenyl-4-yl)-L-alanine methyl ester Stereoisomer B m.p. 83°–85° C.

TLC (ethyl acetate:hexane=30:70) $R_f$=0.17

$^1$H-NMR (200 MHz, $CDCl_3$): $\delta$ (ppm): 7.55–6.62 (m, 13H, 3Ar); 5.83 (d, 1H, NH); 4.91–4.81 (m, 1H, CHCOO); 3.77 (s, 3H, $OCH_3$); 3.68 (s, 3H, $COOCH_3$); 3.10–2.70 (m, 6H, $SCH_2CHCH_2$ and $CH_2$-biphenyl); 2.30 (s, 3H, $CH_3COS$)

$[M-H]^+=506$;

N-[3-phenylcarbonylthio-2-(phenylmethyl)propionyl]-(3'-chloro-1,1'-biphenyl-4-yl)-L-alanine methyl ester m.p. 111°–113° C.

$^1$H-NMR (200 MHz, $CDCl_3$): $\delta$ (ppm): 8.00–6.62 (m, 18H, Ar); 5.89 and 5.71 (2d, 1H, NH); 4.91–4.75 (m, 1H, CHCOO); 3.60 (s, 3H, COOCH$_3$); 3.37–2.61 (m, 7H, CH$_2$CHCH$_2$ and CH$_2$-biphenyl)

[M-H]$^+$=572;

N-[(2S)-3-phenylcarbonylthio-2-(phenylmethyl)propionyl]-(1,1'-biphenyl-4-yl)-L-alanine methyl ester m.p. 138°–140° C.

TLC (ethyl acetate:hexane=3:7) R$_f$=0.25

$^1$H-NMR (200 MHz, CDCl$_3$): δ (ppm): 8.00–7.01 (m, 19H, Ar); 5.75 (d, 1H, NH); 4.85–4.72 (m, 1H, CHCOO); 3.60 (s, 3H, COOCH$_3$); 3.35–2.61 (m, 7H, CH$_2$CHCH$_2$ and CH$_2$-biphenyl)

[M-H]$^+$=538;

N-[(2R)-3-phenylcarbonylthio-2-(phenylmethylpropionyl-(1,1'-biphenyl-4-yl)-L-alanine methyl ester m.p. 156°–158° C.

TLC (ethyl acetate:hexane=1:1) R$_f$=0.5

$^1$H-NMR (200 MHz, CDCl$_3$): δ (ppm): 7.98–6.61 (m, 19H, Ar); 5.89 (d, 1H, NH); 4.92–4.80 (m, 1H, CHCOO); 3.60 (s, 3H, COOCH$_3$); 3.30–2.60 (m, 7H, CH$_2$CHCH$_2$ and CH$_2$-biphenyl)

[M-H]$^+$=538;

N-[2-isopropyl-3-(phenylcarbonylthio)propionyl]-(1,1'-biphenyl-4-yl])-L-alanine methyl ester m.p. 123°–125° C.

$^1$H-NMR (200 MHz, CDCl$_3$): δ (ppm): 7.98–7.07 (m, 14H, Ar); 5.93 (2d, 1H, NH); 5.02–4.87 (m, 1H, CHCOO); 3.71–3.65 (2s, 3H, COOCH$_3$); 3.51–3.00 (m, 4H, S-CH$_2$ and CH-$_2$-biphenyl); 2.28–2.11 (m, 1H, CH-CONH); 2.82–2.02 (m, 1H, S-CH-CH-CH); 1.07 and 0.98 and 0.89 (3d, 6H, CH$_3$-CH-CH$_3$)

[M-H]$^+$=490;

N-[2-phenylcarbonylthiomethyl-3-(3-pyridyl)propionyl]-(1,1'-biphenyl-4-yl)-L-alanine methyl ester—Stereoisomer A m.p. 158°–160° C.

TLC (methylene chloride:methanol=95:5) R$_f$=0.5

$^1$H-NMR (200 MHz, CDCl$_3$): δ (ppm): 8.40–6.75 (m, 18H, Ar); 6.98 (d, 1H, NH); 4.90–4.78 (m, 1H, CHCOO); 3.60 (s, 3H, COOCH$_3$); 3.35–2.65 (m, 7H, CH$_2$CHCH$_2$ and CH$_2$-biphenyl)

[M-H]$^+$=539;

N-[2-phenylcarbonylthiomethyl-3-(3-pyridyl)propionyl]-(1,1'-biphenyl-4-yl)-L-alanine methyl ester—Stereoisomer B m.p. 142°–144° C.

TLC (methylene chloride:methanol=95:5) R$_f$=0.4

$^1$H-NMR (200 MHz, CDCl$_3$): δ (ppm): 8.30–7.02 (m, 18H, Ar); 6.65 (d, 1H, NH); 4.91–4.80 (m, 1H, CHCOO); 3.60 (s, 3H, COOCH$_3$); 3.21–2.65 (m, 7H, CH$_2$CHCH$_2$ and CH$_2$-biphenyl)

[M-H]$^+$=539;

N-[3-(2-furyl)-2-(phenylcarbonylthiomethylpropionyl]-(1,1'-biphenyl-4-yl)-L-alanine methyl ester m.p. 114°–116° C.

$^1$H-NMR (200 MHz, CDCl$_3$): δ (ppm): 7.98–6.00 (m, 18H, Ar and NH); 4.95–4.82 (m, 1H, CHCOO); 3.69–3.62 (2s, 3H, COOCH$_3$); 3.36–2.35 (m, 7H, CH$_2$CHCH$_2$ and CH$_2$-biphenyl)

[M-H]$^+$=528;

N-[3-(3-methyl-5-isoxazolyl)-2-(phenylcarbonylthiomethyl)propionyl]-(1,1'-biphenyl-4-yl)-L-alanine methyl ester—Stereoisomer A m.p. 130°–132° C.

TLC (ethyl acetate:hexane=1:1) R$_f$=0.39

$^1$H-NMR (200 MHz, CDCl$_3$): δ (ppm): 7.92–7.00 (m, 14H, Ar); 6.34 (d, 1H, NH); 5.88 (s, 1H, CH-isoxazolyl); 4.93–4.80 (m, 1H, CHCOO); 3.66 (s, 3H, COOCH$_3$); 3.40–2.80 (m, 7H, CH$_2$CHCH$_2$ and CH$_2$-biphenyl)

[M-H]$^+$=543;

N-[3-(3-methyl-5-isoxazolyl)2-(phenylcarbonylthiomethyl)propionyl]-(1,1'-biphenyl-4-yl-L-alanine methyl ester—Stereoisomer B m.p. 146°–148° C.

TLC (ethyl acetate:hexane=1:1) R$_f$=0.34

$^1$H-NMR (200 MHz, CDCl$_3$): δ (ppm): 7.95–7.10 (m, 14H, Ar); 6.15 (d, 1H, NH); 5.91 (s, 1H, CH-isoxazolyl); 4.95–4.85 (m, 1H, CHCOO); 3.70 (s, 3H, COOCH$_3$); 3.21–2.78 (m, 7H, CH$_2$CHCH$_2$ and CH$_2$-biphenyl)

[M-H]$^+$=543.

N-[(2S)-3-phenyl-2-(phenylcarbonylthio)propionyl]-(1,1'-biphenyl-4-yl)-L-alanine methyl ester m.p. 128°–130° C.

$^1$H-NMR (200 MHz, CDCl$_3$): δ (ppm): 7.82–7.00 (m, 19H, Ar); 6.70 (d, 1H, NH); 4.90–4.80 (m, 1H, CHCOO); 4.41 (t, 1H, CH-S); 3.70 (s, 3H, COOCH$_3$); 3.50–2.93 (m, 4H, CH$_2$CH-Ar and CH$_2$-biphenyl)

[M-H]$^+$=524;

EXAMPLE 2

Preparation of N-(2-mercaptomethyl-3-phenylpropionyl)-(1,1'-biphenyl-4-yl)-L-alanine (Compound 1)

N-[3-phenylcarbonylthio-2-(phenylmethyl)propionyl]-(1,1'-biphenyl-4-yl)-L-alanine phenylmethyl ester (1.84 g; 3 mmoles), prepared as described in example 1, was suspended in ethanol (36 ml), degassed by nitrogen bubbling to eliminate the oxygen.

An aqueous degassed solution of sodium hydroxide 1N (9 ml) was added dropwise at 5° C. to the suspension and, at the end of the addition, further degassed ethanol was added (20 ml). The reaction mixture was kept under stirring for 4 hours at room temperature, then cooled at 0° C. and acidified with hydrochloric acid 5% (10 ml).

The resultant solution was evaporated under reduced pressure and the residue was purified by flash chromatography (silica gel, eluent ethyl acetate:hexane:acetic acid=30:70:5, pressure of nitrogen=0.1 atm) affording a solid which, after treatment with hexane, furnished Compound 1 (1.2 g).

m.p. 108°–110° C.

$^1$H-NMR (200 MHz, CDCl$_3$): δ (ppm): 7.54–6.80 (m, 14H, Ar); 5.90 (d, 1H, J$_{HH}$=7.8 Hz, NH; 4.96–4.83 (m, 1H, CHCOO); 3.30–2.42 (m, 7H, SCH$_2$CHCH$_2$ and CH$_2$-biphenyl); 1.62–1.53 and 1.38–1.29 (m, 1H, SH).

[M-H]$^+$=420

By working in an analogous way the following compounds were prepared:

N-[2-mercaptomethyl-3-(3-methoxyphenyl)propiony]-(1,1'-biphenyl-4-yl)-L-alanine

Stereoisomer A (Compound 2)

m.p. 122°–124° C.

[α]$^{20}$=+55° (c=0.1; CHCl$_3$)

TLC (ethyl acetate:hexane:acetic acid=50:50:5) R$_f$=0.37

$^1$H-NMR (200 MHz, DMSO-d$_6$): δ (ppm): 8.31 (d, 1H, J$_{HH}$=8.1 Hz, NH); 7.62–6.69 (m, 13H, Ar); 4.56–4.45 (m, 1H, CHCOO); 3.69 (s, 3H, OCH$_3$); 3.17–2.20 (m, 7H, SCH$_2$CHCH$_2$ and CH$_2$-biphenyl); 1.84–1.72 (bs, 1H, SH)

[M-H]$^+$=450;

N-[2-mercaptomethyl-3-(3-methoxyphenylpropionyl]-(1,1'-biphenyl-4-yl)-L-alanine

Stereoisomer B (Compound 3)

m.p. 48°–50° C.

[α]$^{20}$=+22.7° (c=0.1; CHCl$_3$)

$^1$H-NMR (200 MHz, DMSO-d$_6$): δ (ppm): 8.31 (d, 1H, J$_{HH}$=8.1 Hz, NH); 7.62–6.63 (m, 13H, Ar); 4.51–4.40 (m, 1H, CHCOO); 3.67 (s, 3H, OCH$_3$); 3.05–2.32 (m, 7H, SCH$_2$CHCH$_2$ and CH$_2$-biphenyl); 2.26–2.08 (bs, 1H, SH)

[M-H]$^+$=450;

N-(2-mercaptomethyl-3-phenylpropionyl)-(3'-chloro-1,1'-biphenyl-4-yl)-L-alanine

Stereoisomer A (Compound 4)

$^1$H-NMR (200 MHz, CDCl$_3$): δ (ppm): 7.49–6.80 (m, 13H, Ar); 5.87 (d, 1H, J$_{HH}$=7.6 Hz, NH); 4.95–4.81 (m, 1H, CHCOO); 3.30–3.00 (m, 2H, CH$_2$-biphenyl); 2.94–2.43 (m, 5H, HS-CH$_2$-CH-CH$_2$); 1.38–1.29 (m, 1H, SH)

[M-H]$^+$=454;

N-(2-mercaptomethyl-3-phenylpropionyl)-(3'-chloro-1,1'-biphenyl-4-yl)-L-alanine

Stereoisomer B (Compound 5)

$^1$H-NMR (200 MHz, CDCl$_3$): δ (ppm): 7.49–6.68 (m, 13H, Ar); 5.93 (d, 1H, J$_{HH}$=7.8 Hz, NH); 4.94–4.85 (m, 1H, CHCOO); 3.12–2.45 (m, 7H, CH$_2$-CH-CH$_2$ and CH$_2$-biphenyl); 1.61–1.52 (m, 1H, SH)

[M-H]$^+$=454;

N-[(2S)-2-mercaptomethyl-3-phenylpropionyl]-(1,1'-biphenyl-4-yl)-L-alanine (Compound 6)

m.p. 160°–162° C.

$^1$H-NMR (200 MHz, CDCl$_3$): δ (ppm): 7.54–7.08 (m, 14H, Ar); 5.84 (d, 1H, J$_{HH}$=7.5 Hz, NH); 4.91–4.82 (m, 1H, CHCOO); 3.25 and 3.07 (ABX, Jab=14.1 Hz, Jax=5.4 Hz, Jbx=7.0 Hz, CH$_2$-biphenyl); 2.95–2.43 (m, 5H, HS-CH$_2$-CH-CH$_2$); 1.38–1.29 (m, 1H, SH)

[M-H]$^+$=420;

N-[(2R)-2-mercaptomethyl-3-phenylpropionyl]-(1,1'-biphenyl-4-yl)-L-alanine (Compound 7)

m.p. 147°–149° C.

$^1$H-NMR (200 MHz, CDCl$_3$): δ (ppm): 7.54–6.79 (m, 15H, Ar and COOH); 5.94 (d, 1H, J$_{HH}$=7.9 Hz, NH); 4.94–4.85 (m, 1H, CHCOO); 3.13–2.43 (m, 7H, HS-CH$_2$-CH-CH$_2$ and CH$_2$-biphenyl); 1.61–1.52 (m, 1H, SH)

[M-H]$^+$=420;

N-[(2S)-2-mercapto-3-phenylpropionyl]-(1,1'-biphenyl-4-yl)-L-alanine (Compound 8)

m.p. 93°–95° C.

$^1$H-NMR (200 MHz, CDCl$_3$): δ (ppm): 8.82 (bs, 1H, COOH); 7.52–7.07 (m, 14H, Ar); 6.82 (d, 1H, J$_{HH}$=7.7 Hz, NH); 4.91–4.82 (m, 1H, CHCOO); 3.63–3.52 (m, 1H, CH-SH); 3.26–3.02 (m, 4H, CH$_2$-biphenyl and CH$_2$-Ar); 1.91 (d, 1H, J$_{HH}$=9.0 Hz, SH)

[M-H]$^+$=406;

N-(2-isopropyl-3-mercaptopropionyl(1,1'-biphenyl-4-yl)-L-alanine (Compound 9)

m.p. 182°–184° C.

$^1$H-NMR (200 MHz, CDCl$_3$): δ (ppm): 7.56–7.27 (m, 9H, Ar); 6.10–6.05 (m, 1H, NH); 5.09–4.91 (m, 1H, CHCOO); 3.63–3.05 (m, 2H, CH$_2$-biphenyl); 2.86–2.45 (m, 2H, CH$_2$-SH); 2.02–1.92 (m, 1H, CH-CH$_2$-SH); 1.91–1.70 (m, 1H, CH$_3$-CH-CH$_3$); 1.60–1.21 (m, 1H, SH); 0.91–0.70 (m, 6H, CH$_3$-CH-CH$_3$)

[M-H]$^+$=372;

N-[2-mercaptomethyl-3-(3-pyridyl)propionyl]-(1,1'-biphenyl-4-yl)-L-alanine hydrochloride Stereoisomer A (Compound 10)

$^1$H-NMR (200 MHz, DMSO-d$_6$): δ (ppm): 8.61–7.67 (m, 5H, pyridyl and CONH); 7.64–7.16 (m, 9H, biphenyl); 4.47–4.37 (m, 1H, CH-CH$_2$-biphenyl); 3.05–2.43 (m, 7H, CH$_2$-CH-CH$_2$ and CH$_2$-biphenyl); 2.26 (m, 1H, SH)

[M-H]$^+$=421;

N-[2-mercaptomethyl-3-(3-pyridyl)propionyl]-(1,1'-biphenyl-4-yl)-L-alanine hydrochloride Stereoisomer B (Compound 11)

m.p. 215°–217° C.

$^1$H-NMR (200 MHz, DMSO-d$_6$): δ (ppm): 8.74–7.85 (m, 5H, pyridyl and CONH); 7.61–7.28 (m, 9H, biphenyl); 4.54–4.42 (m, 1H, CH-CH$_2$-biphenyl); 3.13–2.37 (m, 7H, CH$_2$-CH-CH$_2$ and CH$_2$-biphenyl); 1.86 (m, 1H, SH)

[M-H]$^+$=421;

N-[3-(2-furyl)-2-(mercaptomethyl)propionyl]-(1,1'-biphenyl-4-yl)-L-alanine (Compound 12)

m.p. 137°–140° C.

$^1$H-NMR (200 MHz, CDCl$_3$): δ (ppm): 7.56–7.08 (m, 10H, biphenyl and CH-O); 6.35 (b, 1H, COOH); 6.23–5.96 (m, 3H, CONH and O-CH-CH-CH); 5.00–4.87 (m, 1H, CH-CH$_2$-biphenyl); 3.33–2.43 (m, 7H, CH$_2$-CH-CH$_2$ and CH$_2$-biphenyl); 1.65–1.30 (m, 1H, SH)

[M-H]$^+$=410;

N-[2-mercaptomethyl-3-(3-methyl-5-isoxazolyl) propionyl]-(1,1'-biphenyl-4-yl)-L-alanine Stereoisomer A (Compound 13)

$^1$H-NMR (200 MHz, DMSO-d$_6$): δ (ppm): 12.82 (bs, 1H, COOH); 8.51 (d, 1H, J$_{HH}$=8.0 Hz, NH); 7.65–7.26 (m, 9H, biphenyl); 5.78 [s, 1H, CH(isoxazole)]; 4.53–4.42 (m, 1H, CH-COO); 3.14–2.43 (m, 7H CH$_2$-CH-CH$_2$ and CH$_2$-biphenyl); 2.31 (bt, 1H, SH); 1.99 (s, 3H, CH$_3$-isoxazolyl);

N-[2-mercaptomethyl-3-(3-methyl-5-isoxazolyl) proionyl]-(1,1'-biphenyl-4-yl)-L-alanine Stereoisomer B (Compound 14)

m.p. 215°–217° C.

$^1$H-NMR (200 MHz, DMSO-d$_6$): δ (ppm): 12.81 (bs, 1H, COOH); 8.49 (d, 1H, J$_{HH}$=8.3 Hz, NH); 7.63–7.30 (m, 9H, biphenyl); 6.04 [s, 1H, CH(isoxazole)]; 4.59–4.48 (m, 1H, CH-COO); 3.18–2.33 (m, 7H, CH$_2$-CH-CH$_2$ and CH$_2$-biphenyl); 2.12 (s, 3H, CH$_3$-isoxazolyl); 1.86 (t, 1H, J$_{HH}$=8.5 Hz, SH)

EXAMPLE 3

In vitro evaluation of the pharmacologic activity a) NEP-inhibitory activity

The NEP-inhibitory activity was evaluated in membranes from rat kidney cortex prepared according to the procedure described by T. Maeda et al. in Biochim. Biophys. Acta 1983, 731(1), 115–120.

By working at 0°–4° C., kidneys were removed from male Sprague-Dawley rats weighing approximately 300 g.

Cortex was carefully dissected, finely minced and suspended in a homogenization buffer (10 mM sodium phosphate pH 7.4 containing 1 mM MgCl$_2$, 30 mM NaCl, 0.02% NaN$_3$) 1:15 weight/volume.

The tissue was then homogenized for 30 seconds using an Ultra-Turrax homogenizer.

Approximately 10 ml of homogenate were layered over 10 ml of sucrose (41% weight/volume) and centrifuged at 31200 rpm for 30 minutes at 4° C. in a fixed angle rotor.

The membranes were collected from the buffer/sucrose interface, washed twice with 50 mM TRIS/HCl buffer (pH 7.4) and resuspended into the same buffer for storage. The membranes were stored in small aliquots at −80° C. until use.

The NEP-inhibitory activity was evaluated according to the method described by C. Llorens et al., in Eur. J. Pharmacol., 69, (1981), 113–116, as reported hereinafter.

Aliquots of the membrane suspension prepared as above described (concentration 5 μg/ml of proteins) were preincubated in the presence of an aminopeptidase inhibitor (Bestatin—1 mM) for 10 minutes at 30° C.

[$^3$H][Leu$^5$]-enkephaline (15 nM) and buffer TRIS/HCl pH 7.4 (50 mM) were added in order to obtain a final volume of 100 μl.

Incubation (20 minutes at 30° C.) was stopped by adding HCl 0.1M (100 μl).

The formation of the metabolite [$^3$H]Tyr-Gly-Gly was quantified by chromatography on polystyrene columns (Porapak Q).

The inhibition of the metabolite formation in the membrane preparations treated with the compounds of formula I and with the comparative compounds with respect to the untreated membrane preparations was expressed as IC$_{50}$ (nM) value or as percentage of inhibition at a concentration corresponding to $10^{-7}$M.

b) ACE-inhibitory activity

The ACE-inhibitory activity was evaluated according to the method reported in the literature by B. Holmquist et al., in Analytical Biochemistry 95, 540–548 (1979).

50 μM of ACE (250 mU/ml purified by lung rabbit, EC 3.4.15.1 SIGMA) were preincubated with 50 μl of the compound of formula I or of the reference compound in thermostated cuvettes at 37° C.

The reaction was started by adding furylacryloylphenylalanylglycylglycine 0.8 mM (FAPGG-SIGMA).

Contemporaneously, by using a Beckman DU-50 spectrophotometer provided with a program for calculating delta A/minutes and regression coefficients of the enzyme kinetics curves, the absorbance at 340 nm was recorded in continuo for 5 minutes.

The percentage of the enzyme inhibition in the preparations treated with the compounds of formula I or with the comparative compounds with respect to the untreated preparations was expressed as IC$_{50}$ (nM) value.

As an example, we report in the following table 2 the IC$_{50}$ (nM) values or the percentages of inhibition ($10^{-7}$M) related to the ACE-inhibitory activity and NEP-inhibitory activity of the compounds 1, 2, 6, 7, 9–14 and of Thiorphan, Captopril and RB 105 as comparative compounds.

TABLE 2

ACE-inhibitory and NEP-inhibitory activity of compounds 1–2, 6–7, 9–14, Thiorphan, Captopril and RB 105.

| Compound | ACE-inhibitory activity IC$_{50}$ (nM) | NEP-inhibitory activity | |
|---|---|---|---|
| | | IC$_{50}$ (nM) | % inhibition ($10^{-7}$ M) |
| 1 | 5 | 5 | |
| 2 | 7.5 | 16 | |
| 6 | 2.6 | 1.8 | |
| 7 | 25.3 | 6.1 | |
| 9 | 3.8 | 1.2 | |
| 10 | 13 | 2.9 | |
| 11 | 2 | 13 | |
| 12 | 6 | 3.7 | |
| 13 | 13 | | 94% |
| 14 | 11 | | 76% |
| RB 105 | 5 | 24 | |
| Thiorphan | 99 | 11 | |
| Captopril | 3 | not active | |

The data reported in table 2 show that the compounds of formula I, object of the present invention, are endowed with a significant mixed ACE/NEP inhibitory activity.

Said activity is comparable to the ACE-inhibitory activity of Captopril as well as to the NEP-inhibitory activity of Thiorphan.

Furthermore, the mixed ACE/NEP-inhibitory activity of the compounds of formula I is comparable or better than that of the mixed ACE/NEP-inhibitor RB 105.

We claim:

1. A compound of formula

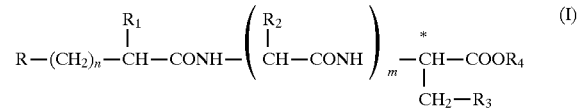

wherein

R is a mercapto group or a R$_5$COS group convertible in the organism to mercapto group;

R$_1$ is a hydrogen atom, a straight or branched C$_1$–C$_6$ alkyl group, an aryl or an arylalkyl group having from 1 to 6 carbon atoms in the straight alkyl moiety wherein the aryl is a phenyl, a biphenyl, a naphthyl, optionally substituted with one or more substituents, the same or different, selected among halogen atoms, hydroxy groups, alkoxy, alkyl, alkylthio, alkylsulphonyl or alkoxycarbonyl groups having from 1 to 6 carbon atoms in the alkyl moiety, C$_1$–C$_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, mono- or di-alkylaminocarbonyl groups having from 1 to 6 carbon atoms in the alkyl moiety;

R$_2$ is a hydrogen atom, a straight or branched C$_1$–C$_6$ alkyl group or an arylalkyl group having from 1 to 6 carbon atoms in the alkyl moiety wherein the aryl is a phenyl, a biphenyl, a naphthyl, optionally substituted with one or more substituents, the same or different, selected among halogen atoms, hydroxy groups, alkoxy, alkyl, alkylthio, alkylsulphonyl or alkoxycarbonyl groups having from 1 to 6 carbon atoms in the alkyl moiety, C$_1$–C$_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, mono- or di-alkylaminocarbonyl groups having from 1 to 6 carbon atoms in the alkyl moiety;

$R_3$ is a biphenyl group optionally substituted with one or more substituents, the same or different, selected among halogen atoms, hydroxy groups, alkoxy, alkyl, alkylthio or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, mono- or di-alkylaminocarbonyl groups having from 1 to 6 carbon atoms in the alkyl moiety;

$R_4$ is a hydrogen atom, a $C_1$–$C_4$ alkyl group or a benzyl group;

$R_5$ is a $C_1$–$C_4$ alkyl group or a phenyl group;

m is 0 or 1;

n is 0 or 1;

the carbon atom marked with an asterisk is a stereogenic centre;

and its pharmaceutically acceptable salts.

2. A compound according to claim 1 wherein $R_3$ is a 4-biphenyl group optionally substituted with from 1 to 3 substituents, the same or different, selected among halogen atoms, hydroxy groups, alkoxy groups and alkyl groups; $R_1$ is a phenylalkyl group optionally substituted with one or more substituents, the same or different, selected among halogen atoms, hydroxy groups, alkoxy groups and alkyl groups; $R_4$ is a hydrogen atom; m is 0 and n is 1.

3. A compound according to claim 1 wherein R is a mercapto group; $R_3$ is 4-biphenyl group optionally substituted with from 1 to 3 substituents, the same or different, selected between fluorine atoms or hydroxy groups; $R_1$ is a phenylmethyl group optionally substituted with one or more substituents, the same or different, selected among halogen atoms, hydroxy groups, alkoxy groups and alkyl groups; $R_4$ is a hydrogen atom; m is 0 and n is 1.

4. A process for the preparation of the compounds of formula

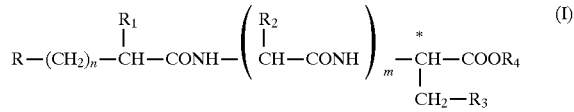

wherein

R, $R_1$, $R_2$, $R_3$, $R_4$, m and n have the meanings reported in claim 1, which comprises the reaction between a compound of formula

wherein

R, $R_1$ and n have the meanings reported in claim 1; and a biphenylalanine derivative of formula

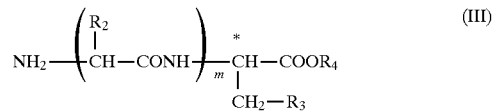

wherein $R_2$, $R_3$, $R_4$ and m have the meanings reported in claim 1.

5. A pharmaceutical composition containing a therapeutically effective amount of a compound according to claim 1 in admixture with a carrier for pharmaceutical use.

6. A pharmaceutical composition according to claim 1 for the treatment of cardiovascular diseases.

7. A method for the treatment of cardiovascular diseases comprising the administration of a therapeutically effective amount of a compound according to claim 1.

\* \* \* \* \*